United States Patent [19]

Konno et al.

[11] Patent Number: 4,960,918
[45] Date of Patent: Oct. 2, 1990

[54] ORGANIC SILICON COMPOUND HAVING A CINNAMILIDENEAMINOPROPYL GROUP

[75] Inventors: Hiroki Konno, Annaka; Yasushi Yamamoto, Takasaki; Shigehisa Sonegawa, Annaka, all of Japan

[73] Assignee: Shin-Etsu Chemical Co., Ltd., Tokyo, Japan

[21] Appl. No.: 410,352

[22] Filed: Sep. 21, 1989

[30] Foreign Application Priority Data

Sep. 22, 1988 [JP] Japan ................................. 63-238524

[51] Int. Cl.$^5$ ............................................... C07F 7/10
[52] U.S. Cl. ................................................... 556/425
[58] Field of Search ........................................... 556/425

[56] References Cited

U.S. PATENT DOCUMENTS

| | | | |
|---|---|---|---|
| 2,942,019 | 6/1960 | Oike et al. | 556/425 X |
| 3,022,270 | 2/1962 | Lisenke | 556/425 X |
| 4,321,394 | 3/1982 | Schäfer et al. | 556/425 X |
| 4,866,152 | 9/1989 | Lo | 556/425 X |

*Primary Examiner*—Paul F. Shaver
*Attorney, Agent, or Firm*—Oblon, Spivak, McClelland, Maier & Neustadt

[57] ABSTRACT

The novel organic silicon compound of the present invention is represented by the general formula:

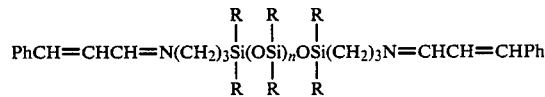

wherein R is an alkyl group having 1 to 3 carbon atoms, n is an integer of 0 to 10. This organic silicon compound has a feature in structure where cinnamilideneaminopropyl groups are introduced into both terminals of the siloxane chain, and this compound is useful as a vulcanizing agent for fluororubbers.

5 Claims, 2 Drawing Sheets

ORGANIC SILICON COMPOUND HAVING A CINNAMILIDENEAMINOPROPYL GROUP

BACKGROUND OF THE INVENTION

1. Field of the Invention

This invention relates to a novel organic silicon compound having a cinnamilideneaminopropyl group, and particularly to an organic silicon compound which is useful as a vulcanizing agent for fluororubbers.

2. Description of the Prior Arts

Heretofore, N,N'-cinnamilidene-1,6-hexadiamine is known as a vulcanizing agent for fluororubbers, which is represented by the following formula:

PhCH=CHCH=N(CH$_2$)$_6$N=CHCH=CHPh

Generally, a fluororubber is inferior in processability, such as roll workability, and the cured rubber obtained therefrom has a high minimum rubber-state temperature, so that the cured rubber is inferior in low-temperature properties which are determined by, for example, a Gehman torsion test.

SUMMARY OF THE INVENTION

The present inventors have found that an organic silicon compound having a cinnamilidene-aminopropyl group and a siloxane chain which is a novel substance provided by the present invention is useful as a vulcanizing agent for fluororubbers, and that the compound enhances the processability, such as roll workability, of the fluororubbers. Since the compound has a siloxane chain, it is expected that the low-temperature properties of the fluororubbers after cure will be improved.

Thus, the present invention provides an organic silicon compound represented by the general formula (I):

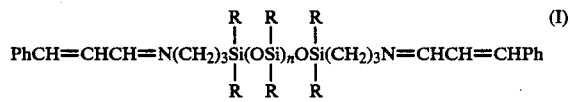

wherein R is an alkyl group having 1 to 3 carbon atoms, n is an integer of 0 to 10.

DETAILED DESCRIPTION OF THE PREFERRED EMBODIMENTS OF THE INVENTION

Figure 1:
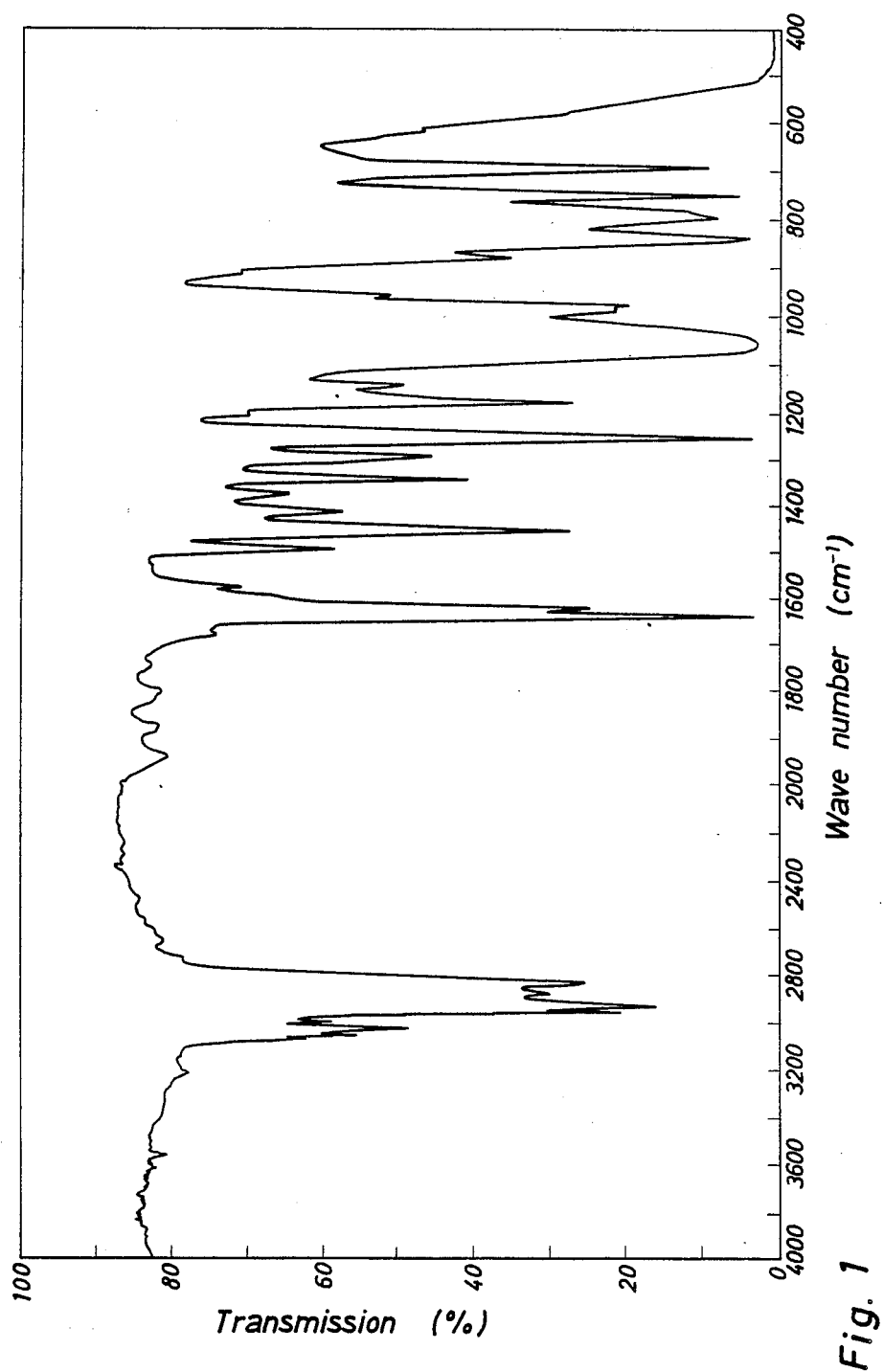
FIG. 1 shows an infrared absorption spectrum of an organic silicon compound obtained in Example 1.

When the organic silicon compound is used as a vulcanizing agent for fluororubbers, n in the general formula (I) has relation with the number of crosslinking points per unit amount of the compound to be blended. If n is larger than 10, the amount must be increased to guarantee a predetermined number of crosslinking points, and the properties of the fluororubbers to be obtained after cure are liable to be impaired. Accordingly, n is suitably in the range of 0 to 10, and preferably 0 to 3, and it is particularly preferable that n is 0, 1 or 2.

R in the general formula (I) is an alkyl group of 1 to 3 carbon atoms, and in view of a practical use and production, R typically include a methyl group and an ethyl group. A methyl group is preferable also in use as a vulcanizing agent.

Namely, the most preferred organic silicon compound in the present invention is represented by the following general formula:

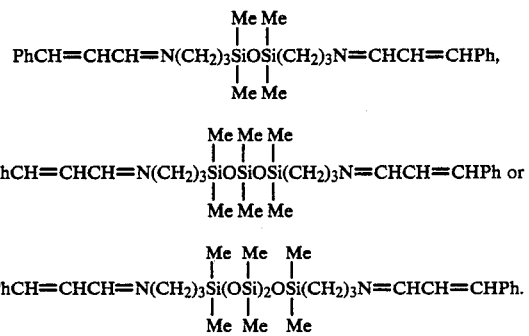

The organic silicon compound of the present invention can be synthesized by the reaction of α, ω-bisaminopropylsiloxane represented by the general formula (II):

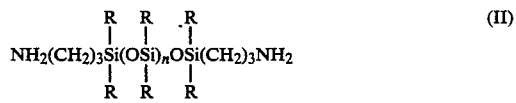

wherein R and n are as defined above, with cinnamaldehyde represented by the general formula (III):

PhCH=CHCHO                (III)

at usually 0 to 100° C., and preferably 20 to 60° C. If the reaction temperature is too low, the rate of the reaction is slow, while if it is too high, the organic silicon compound produced is likely to be decomposed at the imine moiety thereof. Usually, the reaction may be carried out by adding cinnamaldehyde of the general formula (III) to aminosiloxane of the general formula (II) dropwise.

Generally, the above reaction is sufficiently carried out without a solvent, but a solvent may be used for the reaction. As the solvent, a non-proton type solvents incompatible with water are preferred, and especially solvents containing no halogen are preferred. Examples of the solvent include a hydrocarbon, such as benzene, toluene, xylene, pentane, hexane and cyclohexane; and an ether such as anisole and dibutyl ether.

The so-obtained organic silicon compound having a cinnamilideneaminopropyl group is a novel compound and is unknown heretofore.

The organic silicon compound is useful, for example, as a vulcanizing agent for fluororubbers. If the compound is used as the vulcanizing agent for fluororubbers, it can be expected that the processability such as roll workability of the fluororubbers is improved and the low-temperature properties of cured rubbers to be obtained are also improved.

The present invention will now be described below in more detail with reference to Examples.

EXAMPLE 1

74.4 g (0.3 mole) of 1,3-bis(3-aminopropyl)-1,1,3,3-tetramethyldisiloxane was charged into a four-necked flask, and then a gas replacement was conducted with nitrogen gas. Into the flask was added dropwise 79.2 g (0.6 mole) of cinnamaldehyde over 0.5 hours. After the adding, the reaction mixture was stirred for another 2 hours at 40 to 50° C. After the reaction, water produced on the reaction and other volatile substances were removed under the condition of 60 to 70° C./1mmHg, and 91 g (96% yield) of 1,3-bis(3-cinnamilideneamino) propyl-1,1,3,3-tetramethyldissiloxane was thereby obtained.

The compound was identified as the above substance by the following data obtained from measurement.

[Infrared absorption spectrum]

The infrared absorption curve measured on the compound isshown in FIG. 1. Characteristic absorptions:

1640 cm$^{-1}$ (N=CH)

1625 cm$^{-1}$ (CH=CH)

1255 cm$^{-1}$ (SiMe)

1060 cm$^{-1}$ (Si)Si)

[NMR spectrum]
(solventless, internal standard: cyclohexane)

7.70–7.40 (m, 2H, —CH=N—)

7.30–6.70 (m, 10H, aromatic ring proton)

6.58–6.38 (m, 4H, —CH=CH—)

3.40–3.02 (t, 4H, =N—CH$_2$—)

1.74–1.22 (m, 4H, —C—CH$_2$—C—)

0.60–0.20 (m, 4H, —C—CH$_2$—Si)

−0.04 (s, 12H, SiMe)

[Elemental analysis]%:

|  | C | H | Si |
|---|---|---|---|
| Calculated: | 70.5 | 8.5 | 11.8 (as C$_{28}$H$_{40}$N$_2$OSi$_2$) |
| Found: | 69.5 | 8.7 | 11.0 |

EXAMPLE 2

Reaction was conducted in the same manner as in Example 1 except that 53 g (0.16 mole) of 1,5-bis(3-aminopropyl)-1,1,3,3,5,5-hexamethyl-1,3,5-tris iloxane and 42.2 g (0.32 mole) of cinnamaldehyde were used as reactants, so that 85 g (97% yield) of 1,5-bis(3-cinnamilideneamino)propyl-1,1,3,3,5,5-hexamethyltrisiloxane was obtained.

The compound was identified as the above substance by the following data obtained from measurement.

[Elemental analysis]%:

|  | C | H | Si |
|---|---|---|---|
| Calculated: | 65.4 | 8.4 | 15.3 (as C$_{30}$H$_{46}$N$_2$O$_2$Si$_3$) |
| Found: | 64 | 9 | 14 |

[Infrared absorption spectrum]
Characteristic absorptions:

1640 cm$^{-1}$ (—N=CH—)

1620 cm$^{-1}$ (—CH=CH—)

1255 cm$^{-1}$ (SiMe)

1045 cm$^{-1}$ (SiOSi)

[NMR spectrum]
(solventless, internal standard: cyclohexane)

7.90–7.56 (m, 2H, —CH=N)

7.63–6.83 (m, 10H, aromatic ring proton)

6.73–6.43 (m, 4H, —CH=CH—)

4.23–3.00 (t, 4H, —NCH$_2$—CH)

2.00–0.83 (m, 4H, —C—CH$_2$—C—)

0.8–0.13 (m, 4H, —C—CH$_2$—Si—)

0.04 (s, 12H, (CH$_2$)$_3$SiCH$_3$)Si)

0.07 (s, 6H, SiOSi(CH$_3$)$_2$Si)

EXAMPLE 3

The procedures of Example 1 was repeated except that 109 g (0.2 mole) of a siloxane having 3-aminopropyl groups at both terminals thereof and represented by the general formula:

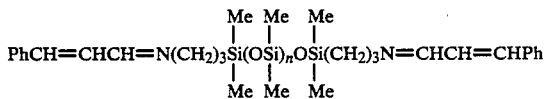

wherein n is 4 on average,
and 52.8 g (0.4 mole) of cinnamaldehyde were used as reactants, so that 147 g (95% yield) of the siloxane having 3-cinnamilideneaminopropyl groups at both terminals thereof and represented by the general formula:

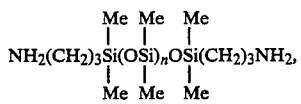

wherein n is 4 on average, were obtained.

The compound was identified as the above substance by the following data obtained from measurement.

[Elemental analysis] %:

|  | C | H | Si |
|---|---|---|---|
| Calculated: | 54.5 | 8.6 | 22.5 (as C$_{34}$H$_{64}$N$_2$O$_5$Si$_6$) |
| Found: | 52 | 9 | 20 |

[Infrared absorption spectrum]
Characteristic absorptions:

1640 cm$^{-1}$ (—N=CH—)

1625 cm$^{-1}$ (—CH=CH—)

1260 cm$^{-1}$ (SiMe)

1100–1020 cm$^{-1}$ (SiOSi)

[NMR spectrum]
(solventless, internal standard: cyclohexane)

7.90–7.53 (m, 2H, —CH=N—)

7.37–6.77 (m, 10H, aromatic ring proton)

6.83–6.37 (m, 4H, —CH=CH—)

3.53–3.00 (t, 4H, =N—CH$_2$—)

1.90–0.90 (m, 4H, C—CH$_2$—C)

0.77–0.17 (m, 4H, —C—CH$_2$Si)

—0.13 (s, 36H, SiMe)

—0.07 (s, 6H, SiOSi(CH$_3$)$_2$SI)

EXAMPLE 4

A fluororubber was vulcanized in the following procedure using the organic silicon compound obtained in Example 1 as a vulcanizing agent.

To 100 parts by weight of a commercially available fluororubber VITON B-50 (manufactured by Du Pont Co., Ltd.), were successively added 20 parts by weight of MT-Carbon (tradename: N-990, manufactured and sold by Can Carf Co., Ltd.), 15 parts by weight of magnesium oxide (KYOWAMAG #30, manufactured and sold by Kyowa Chemical Co., Ltd.), and 4 parts by weight of the organic silicon compound obtained in Example 1, and the components were then blended with a two-roll rubber kneading mill. The vulcanization state of the obtained blend was investigated by measuring change of torque at 175° C. using a disk-rheometer ODR-100 (Toyo Seiki Co., Ltd.).

Figure 2:
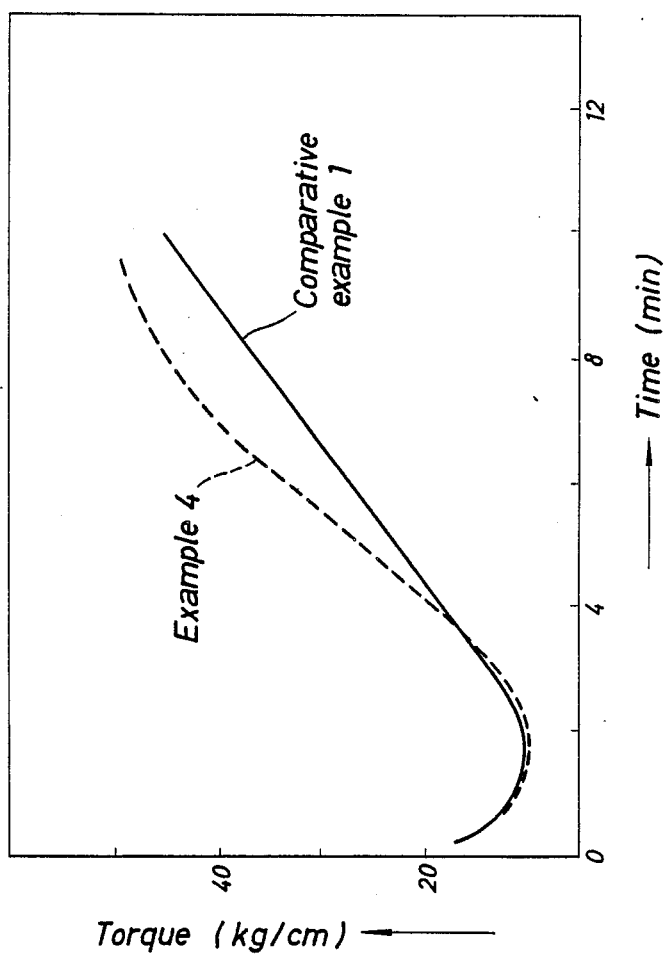
FIG. 2 shows a result test in Example 4 and Comparative Example.

The result is shown in FIG. 2.

COMPARATIVE EXAMPLE 1

Vulcanization of a fluororubber was carried out in the same manner as Example 4 except that 3 parts by weight of N,N'-dicinnamilidene-1,6-hexanediamine per 100 parts by weight of a fluororubber VITON B-50 (manufactured and sold by Du Pont Co., Ltd.) was used in place of the organic silicon compound of Example 1.

The result is shown in FIG. 2.

EXAMPLES 5 and 6 AND COMPARATIVE EXAMPLE 2

In Example 5, Example 6 and Comparative Example 2, the organic silicon compound produced in Example 2, the organic silicon compound produced in Example 3 or N,N'-dicinnamilideneamino-1,6-hexamethylenediamine, Diak No. 3 (tradename, supplied by Du Pont, Co., Ltd.) was used, respectively, as a vulcanizing agent in an amount as shown in Table 1 per 100 parts by weight of a fluororubber, DAIEL G-201 (tradename, supplied by Daikin Industries Ltd.). In each example, to the fluororubber were successively added various components in the amounts as shown in Table 1, while the mixture was thoroughly kneaded with a two-roll kneading mill, to give a composition.

The composition thus obtained was vulcanized under the conditions given in Table 1 with being formed under pressure by means of a press. Thereafter, the composition was vulcanized under heating in a heat furnace to produce a sheet composed of a vulcanized rubber.

In the operation of the above pressing, the press workability was evaluated in accordance with the standard given below.

Further, the sheet obtained was subjected to a low-temperature torsion test in accordance with the method set out below.

The results are given in Table 1.

Roll workability

The composition is roll worked under the conditions of a roll interval of 3 mm and a rolling time of 20 min./batch. The number of cross blending operations which can be conducted to the composition during the above roll working is measured. Also, the mixing state of the filler and the adherability of the composition being worked to the roll surfaces were observed. From these, the roll workability was evaluated in accordance with the following standards.

A: The cross blending operation could be carried out over 40 times.

Mixing state: Good.

No adhesion to roll was recognized.

B: The cross blending operation could be carried out 25 to 40 times.

Mixing state: A layer of the filler was recognized on the surface.

Tendency of adhesion to the roll surface was recognized during the working, and the roll releasability was not good.

C: The cross blending operation could be carried out at most 25 times only.

Mixing state: A thick layer of the filler was recognized at the surface.

Adhesion to the roll surface occurred during the working, and the rolls had to be stopped during the rolling; therefore the roll surface had to be cooled.

Moreover, the degree of stain of the roll surface after the kneading, was evaluated in accordance with the following standard by observing how easy the filler could be removed from the roll surface.

A: The filler can be easily removed only by wiping with gauze.

B: The filler can be removed when it is wiped with force.

C: The filler can be removed only when it is wiped with an abrasive material.

Press workability

The press workability was evaluated in accordance with the following standard.

A: It is easy to weigh the composition, arrange its shape into the one to be easily formed under pressure, and release the press-formed one from the mold.

B: Although not easy, it is possible somehow to weigh the composition, arrange its shape into the one to be easily press-formed, and release the press-formed one from the mold.

C: It is difficult to arrange the shape of the composition into the one to be easily press-formed, and releasability of the press-formed one from the mold is entirely bad.

Low-temperature torsion test

A torsion-temperature curve was obtained using a Gehman's torsion tester (TM-502 Model, manufactured and sold by Ueshima Seisakusho Co., Ltd.) and a torsion wire having a torsion constant of 0.500 gf.cm/degree in the ethanol-dry ice, in accordance with JIS K6301. From the curve, $T_2$, $T_5$, $T_{10}$ and $T_{100}$ were determined, at which the specific modulus of a test sample was 2, 5, 10 and 100 respectively.

TABLE 1

|  |  | Example | | Comparative |
|---|---|---|---|---|
|  |  | 5 | 6 | Example 2 |
| Components | | | | |
| Fluoroelastomer *1 | (parts) | 100 | 100 | 100 |
| Organic silicon compound *2 | | | | |
| Blending amount | (parts) | 100 | 100 | — |
| The number of n | | 1 | 4 | — |
| Magnesium oxide | (parts) | 15 | 15 | 15 |
| MT-carbon black | (parts) | 20 | 20 | 20 |
| Diak No. 3 *3 | (parts) | — | — | 3 |
| Vulcanizing condition | | | | |
| Press Vulcanizing | Temperature [°C.] | 175 | 175 | 160 |
|  | Time [min] | 15 | 15 | 15 |
| Heat Vulcanizing | Temperature [°C.] | 200 | 200 | 200 |
|  | Time [min] | 24 | 24 | 24 |
| Processability | | | | |
| Roll workability | | A | A | C |
| Stain after the roll working | | A | A | C |
| Press workability | | A | A | B |

Remarks
*1: DAIEL G-201 manufactured and sold by Daikin Industries Ltd.
*2: Example 5, organic silicon compound produced in Example 2 Example 6, organic silicon compound produced in Example 3
*3: N,N'-dicinnamilideneamino-1,6-hexamethylenediamine manufactured and sold by Du Pont Co., Ltd.

TABLE 2

|  |  | Example | | Comparative |
|---|---|---|---|---|
|  |  | 5 | 6 | Example 2 |
| $T_2$ | [°C.] | −5.5 | −6.6 | −9.2 |
| $T_5$ | [°C.] | −12.0 | −12.4 | −12.4 |
| $T_{10}$ | [°C.] | −14.3 | −14.9 | −14.6 |
| $T_{100}$ | [°C.] | −20.7 | −19.8 | −19.9 |

We claim:

1. An organic silicon compound represented by the general formula (I):

wherein R is an alkyl group having 1 to 3 carbon atoms, n is an integer of 0 to 10.

2. An organic silicon compound according to claim 1, wherein R in the general formula (I) is a methyl group.

3. An organic silicon compound according to claim 2, which is represented by the general formula:

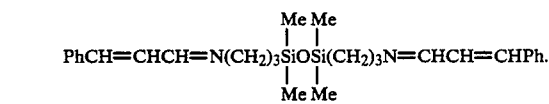

4. An organic silicon compound according to claim 2, which is represented by the general formula:

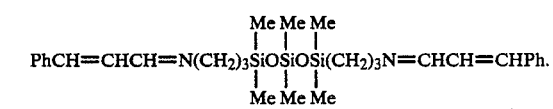

5. An organic silicon compound according to claim 2, which is represented by the general formula:

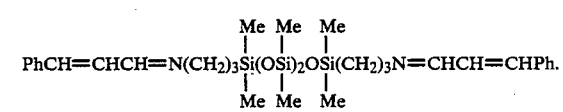

* * * * *